(12) United States Patent
Goetz et al.

(10) Patent No.: US 10,493,573 B2
(45) Date of Patent: Dec. 3, 2019

(54) EXPANDABLE MEDICAL IMPLANT

(71) Applicant: VENUS MEDTECH (HANGZHOU), INC., Hangzhou (CN)

(72) Inventors: Wolfgang Goetz, Regensburg (DE); Hou-Sen Lim, Singapore (SG)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 320 days.

(21) Appl. No.: 15/294,091

(22) Filed: Oct. 14, 2016

(65) Prior Publication Data

US 2017/0028518 A1 Feb. 2, 2017

Related U.S. Application Data

(62) Division of application No. 13/579,918, filed as application No. PCT/EP2011/000738 on Feb. 16, 2011, now abandoned.

(60) Provisional application No. 61/306,564, filed on Feb. 22, 2010.

(30) Foreign Application Priority Data

Feb. 17, 2010 (DE) .......................... 10 2010 008 382

(51) Int. Cl.
*B23P 11/00* (2006.01)
*A61F 2/95* (2013.01)
*A61F 2/24* (2006.01)

(52) U.S. Cl.
CPC .......... *B23P 11/005* (2013.01); *A61F 2/2418* (2013.01); *A61F 2/2439* (2013.01); *A61F 2/95* (2013.01); *A61F 2/2412* (2013.01); *A61F 2002/9511* (2013.01); *A61F 2002/9522* (2013.01); *A61F 2250/0073* (2013.01); *Y10T 29/49908* (2015.01); *Y10T 29/53709* (2015.01)

(58) Field of Classification Search
CPC .... B23P 11/005; A61F 2/2418; A61F 2/2439; A61F 2/95; A61F 2002/9511; A61F 2250/0073; A61F 2/2412; A61F 2002/9522; Y10T 29/49908; Y10T 29/53709

See application file for complete search history.

(56) References Cited

U.S. PATENT DOCUMENTS

| | | |
|---|---|---|
| 3,657,744 A | 4/1972 | Ersek |
| 5,282,824 A | 2/1994 | Gianturco |
| 5,546,646 A | 8/1996 | Williams et al. |
| 5,693,083 A | 12/1997 | Baker |
| 5,951,540 A * | 9/1999 | Verbeek .................. A61F 2/958 606/1 |
| 6,183,503 B1 | 2/2001 | Hart et al. |

(Continued)

FOREIGN PATENT DOCUMENTS

| | | |
|---|---|---|
| EP | 2033593 | 3/2009 |
| JP | 63123675 | 5/1988 |

(Continued)

*Primary Examiner* — Robert A Lynch
*Assistant Examiner* — Michael G Mendoza
(74) *Attorney, Agent, or Firm* — Raymond Sun

(57) ABSTRACT

A method for crimping a medical implant includes at least one foldable and/or unfoldable structure on or around or over a portion or outer surface of a catheter or of a catheter tip. No pressure beyond a predetermined pressure is exerted on the structure during and/or after crimping of the implant.

8 Claims, 3 Drawing Sheets

(56) References Cited

U.S. PATENT DOCUMENTS

| | | |
|---|---|---|
| 6,241,760 B1 | 6/2001 | Jang |
| 6,651,478 B1 | 11/2003 | Kokish |
| 2004/0078953 A1* | 4/2004 | Spilka .................. A61F 2/958 29/505 |
| 2004/0123437 A1 | 7/2004 | Kokish |
| 2004/0128818 A1 | 7/2004 | Motsenbocker |
| 2005/0154450 A1 | 7/2005 | Larson et al. |
| 2006/0004469 A1 | 1/2006 | Sokel |
| 2007/0162102 A1* | 7/2007 | Ryan .................. A61F 2/958 623/1.12 |
| 2007/0289117 A1 | 12/2007 | Huang et al. |
| 2008/0154355 A1 | 6/2008 | Benichou et al. |
| 2009/0005863 A1* | 1/2009 | Goetz .................. A61F 2/2418 623/2.18 |
| 2009/0299453 A1 | 12/2009 | Arcand et al. |
| 2010/0234940 A1* | 9/2010 | Dolan .................. A61F 2/2433 623/2.11 |
| 2011/0040366 A1 | 2/2011 | Goetz et al. |

FOREIGN PATENT DOCUMENTS

| | | |
|---|---|---|
| JP | 11332996 | 12/1999 |
| JP | 11332997 | 12/1999 |
| JP | 2007-517587 | 7/2007 |
| JP | 2007517587 | 7/2007 |
| JP | 2008503264 | 2/2008 |
| JP | 2009507567 | 2/2009 |
| JP | 2009540928 | 11/2009 |
| JP | 2011526162 | 10/2011 |
| WO | 2007/149464 | 11/2003 |
| WO | 2005/070335 | 8/2005 |
| WO | 2007149464 | 12/2007 |
| WO | 2008/029296 | 3/2008 |
| WO | 2008029296 | 3/2008 |
| WO | 2009/026272 | 2/2009 |
| WO | 2009026272 | 2/2009 |
| WO | 2009/109348 | 9/2009 |
| WO | 2009109348 | 9/2009 |
| WO | 2010000079 | 1/2010 |

* cited by examiner

EXPANDABLE MEDICAL IMPLANT

CROSS-REFERENCE TO RELATED APPLICATION

This application is a divisional application of U.S. application Ser. No. 13/579,918, filed Dec. 27, 2012, the contents of which are incorporated herein by reference.

The present invention relates to a method for crimping of a medical implant onto a delivery implement such as a catheter. The invention further relates to an implant, and also to a delivery device and a crimping device.

In a number of patients, certain body functions have to be carried out or supported by means of technical devices temporarily or permanently disposed to that end ("implanted") in the patient's body.

Quite frequently, implants are delivered to the implantation site within the body by means of a catheter. This is particularly true for implants that are implanted within the body vessel system including the heart itself.

In such cases, the implant is being crimped onto the catheter and released from the latter at the implantation site.

Obviously, since upon crimping remarkable mechanical forces are applied on the implant and also on certain structures implanted together with and fixed to the implant, the crimping process has some influence on the integrity of the crimped implant.

Therefore, it is one object of the present invention to provide an additional crimping method. According to another aspect of the present invention, an implant and a delivery implement are to be provided.

The object of the invention is solved by means of a method as disclosed.

Accordingly, a method for crimping a medical implant comprising at least one foldable or collapsible or crimpable and unfoldable or expandable structure (therefore also referred to as structures) on or around or over a portion or outer surface of a catheter or of a catheter tip or of any other delivery implement or device or part thereof is proposed. The method comprises the feature that no pressure is exerted on the structure during and/or after crimping of the implant beyond a predetermined pressure.

The implant according to the invention is crimped onto the catheter using the method according to the invention.

It comprises at least one implant according to the invention.

Accordingly, the crimping device for crimping of an implant comprising at least one foldable and unfoldable structure on or around or over a portion or outer surface of a catheter or of a catheter tip with a predetermined pressure exerted on the structure.

Embodiments can include one or more of the following features.

In some embodiments according to the method according to the invention, in the context of the present invention the term "crimping a medical implant" may mean the crimping result achieved after termination of the entire crimping process of the medical implant.

In the context of the present invention the term "crimping a medical implant" may mean that the implant crimped by using the method according to the invention is to be understood as prepared on the catheter or delivery implement or device to be inserted or implanted In certain embodiments according to the method according to the invention, in the context of the present invention the term "crimping a medical implant" may mean that additional or further crimping it not necessary or not contemplated or not required before implanting of the implant.

In some embodiments according to the method according to the invention, in the context of the present invention the term "predetermined pressure" may refer to a pressure value that has been determined and/or considered and/or selected by the person responsible for the crimping process or carrying out the same before or during the crimping process takes place.

In certain embodiments of the method according to the invention, in the context of the present invention the term "predetermined pressure" may refer to a pressure value adjusted at a crimping device. The value can preferably be adjusted as a maximum pressure value exerted on certain structures of the implant, for example, heart valve replacement leaflets or commissures thereof.

In some embodiments of the method according to the invention, in the context of the present invention the term pressure exerted "during and/or after crimping of the implant" may refer to pressure exerted by means of the crimping itself.

In particular embodiments of the method according to the invention, the method comprises the step of measuring the pressure acting on or in the structure, or between the structure and other parts of the implant, or between the structure and the delivery device (in particular, the circumferential surface or a section thereof of the delivery device), and the step of terminating the crimping procedure once the pressure measured has reached the predetermined pressure or exceeds the predetermined pressure. In some of these embodiments, the method comprises placing a pressure or force sensor in direct contact with the structure.

In certain embodiments of the method according to the invention, in the context of the present invention the term "predetermined pressure" may refer to a pressure that exclusively results from the crimping steps as such. In those embodiments, pressure exerted on the structures at issue stemming or originating from other pressure sources than by the crimping steps is not referred to as the predetermined pressure. Such other pressure comprises the atmospheric pressure, water or fluid pressure, and the like. In certain embodiments, such additional pressure does not contribute to the determined pressure or the level thereof.

In some embodiments of the method according to the present invention a predetermined pressure may be understood as a predetermined force, strain, stress and the like as well. Hence, in those embodiments, the terms pressure, force, strain, stress and the like may be understood as interchangeable.

In certain embodiments according to the invention, the predetermined pressure is to be understood as a maximally allowable pressure that is measured or may be measured between the structure of the implant and a circumferential surface or an envelope of the delivery device, or equals the such measured pressure.

In some embodiments, the foldable and unfoldable structure is one or more heart valve leaflets or commissures or replacements or substitutes thereof or comprises those.

In certain embodiments, the structure is not the proximal or the distal ring of the implant.

In some embodiments, the structure on the implant is not intended to contribute to the temporary fixation of the implant on the delivery implement/device.

In certain embodiments, the implant comprises one or more interconnecting elements, and the pressure exerted or applying on the structure is determined between the interconnecting elements and the outer surface or the portion of the catheter.

The interconnecting elements may be embodied as posts interconnecting a proximal and a distal ring or support structure.

The interconnecting elements may be embodied as radially (as regards a longitudinal axis of the implant or of the delivery device) expandable or shiftable structures, of the implant, wherein they are expanded or shifted or moved away from the upon expansion of implant.

The interconnecting elements may be embodied as one or more posts.

The interconnecting elements may be embodied as structures provided for maintaining a distance between a distal ring and a proximal ring of the implant.

In some embodiments, the predetermined pressure is 0 N per square millimetre (0 N/mm$^2$) or 1 N/mm$^2$ or 2 N/mm$^2$ or 3 N/mm$^2$ or 5 N/mm$^2$. If the predetermined pressure is 0 N/mm$^2$ or about 0 N/mm$^2$, the method according to the invention may be called a "zero pressure crimping" method.

In certain embodiments, the predetermined pressure is 5 N per square millimetre (5 N/mm$^2$) or 8 N/mm$^2$ or 10 N/mm$^2$ or 15 N/mm$^2$ or 20 N/mm$^2$ or 25 N/mm$^2$ or 30 N/mm$^2$ or any value in between. In some embodiments, the method according to the invention is carried out manually by the aid of non-electric tools.

In certain embodiments, the method according to the invention is carried out by the aid of automatic tools. Such tools can be electric, pneumatic, hydraulic tools and the like.

In some embodiments, the crimping device for crimping of an implant comprising at least one foldable and unfoldable structure on or around or over a portion or outer surface of a catheter or of a catheter tip, comprises a pressure limiting means for limiting the pressure that is exerted or exertable on the implant and/or on the structure during and/or after crimping of the implant.

In certain embodiments, the pressure (or force) exerted or exertable on the structure may be known once the pressure (or force) exerted on the implant comprising the structure is known. For example, it might be known—e.g. from known relationships between a first and a second pressure as defined in the following—that zero pressure (being one example of a first pressure) is applied on the structure if less than a certain pressure (second pressure) is exerted on the implant during crimping. In those embodiments, it may be sufficient to limit the (second) pressure applied to the implant. As may be known in that case from earlier experiments or from a look-up-table, the (first) pressure applied to the structures or acting on the structures in question will then not be higher than a predetermined pressure or a pressure considered to be a maximum pressure that is allowed to apply to the structure.

In some embodiments, the crimping device comprises a pressure sensor (or is functionally linked with it) that reflects the pressure or force exerted on the structure at issue (e.g., the leaflets comprised by the implant) during crimping. Preferably, the pressure sensor is placed, for example, between the structure at issue (such as the leaflets of the implant) and a neighbouring structure (such as an outer surface or other part of the catheter used). In certain embodiments, such a pressure sensor or any other suitable sensor is provided with the catheter. In some embodiments, the pressure sensor or any other suitable sensor is located within a lumen of the catheter or on an outer surface thereof.

In certain embodiments, the crimping device is intended and/or configured for crimping by means of a predetermined pressure exerted on the structure during and/or after crimping of the implant.

In some embodiments, the crimping device comprises a controller for limiting or controlling the pressure exerted on the structure of the implant.

In certain embodiments, the crimping device comprises an adjusting means for adjusting the pressure exerted upon crimping. The adjusting means may be connected to the controller.

In some embodiments, the crimping device is intended and/or configured for crimping medical implants, in particular for crimping only medical implants.

In certain embodiments, the crimping device comprises one or more pressure sensors that output a signal indicating the pressure applied on the structures at issue during crimping.

The implant according to the invention may be of an expandable and again foldable or collapsible, respectively, type. Such implants may, for example, be changed in its diameter by means of strings guided around certain portions of the implant that can be tightened or released. The features required to be amendable in diameter are not in the main focus of the present invention. Since they are further explained in great detail in WO 2008/029296 A2 ("Minimally invasive heart valve replacement", filed on Feb. 15, 2007) to the inventors of the present invention, and also in WO 2009/109348 A1 ("Stent, welcher vom expandierten Zustand kontrolliert erneut im Durchmesser verringerbar ist", filed on Mar. 2, 2009) also to the inventors of the present invention, for the sake of avoiding repetition it is referred to those documents as regards those features. The respective disclosure is herewith incorporated into the present application by way of reference. The same applies to any material mentioned in either of both applications.

Whenever reference is made within the present specification to a catheter, it is to be noted that the term "catheter" is used by way of example for a delivery implement or device for delivering the implant to the implantation site. Hence, the present invention is not to be understood to relate only to catheters—rather, any suitable device for advancing an implant to its implantation site is also contemplated by the inventors.

Along with advantages that are obvious to the skilled one, the embodiments may provide one or more of the following advantages.

Although crimping of implants, in particular stents, is well-known in the art and probably the most often used method for temporarily fixing an implant on a catheter, according to the findings of the inventors the implant or structures comprised by the implant are frequently adversely compressed and sometimes even damaged. Those damages have hitherto not been realized neither by the skilled ones nor by the public. The present inventors, however, realized a problem resulting from applying undue pressure on, e.g., the leaflets of a heart valve replacement such as the one described in above mentioned WO 2008/029296 A2. It appears that the damages observed resulted from a pressure applied on the leaflet and the commissures upon crimping between the interconnecting elements or posts and the sleeve, respectively, on the one side, and the crimping surface (outer surface) of the catheter on the other side.

In some embodiments, it is proposed to carry out the method according to the present invention by advantageously making use of a new implant design providing for space (the first gap) between the interconnecting elements and the catheter to allow, e.g., the commissures of above implant of the figures or other structures to be located between the interconnecting elements and the catheter surface without being pressed or even damaged.

Further, in certain embodiments, it is proposed to carry out the method according to the present invention by advantageously making use of another new design of the implant that provides for sufficient space (second gap) for structures such as the leaflets of the implant of WO 2008/029296 A2 between a sleeve (if provided) or the vessel wall during delivery of the implant, and the surface of the relatively hard and inelastic catheter.

In some embodiments, crushing of leaflets of a valve replacement comprised by the implant may be advantageously avoided.

In certain embodiments, a disruption of collagen fibres found by the inventors of the present invention within leaflets of a valve replacement of natural origin (bovine, for example) after having been crimped can advantageously be prevented.

Other aspects, features, and advantages will be apparent from the description, figures and claims.

In the following, the invention is further explained by means of the figures of the drawing. However, the invention must not be limited to the examples explained by means of the figures. It is noted that within the attached drawing identical reference numeral denote identical or similar structures.

Figure 1:
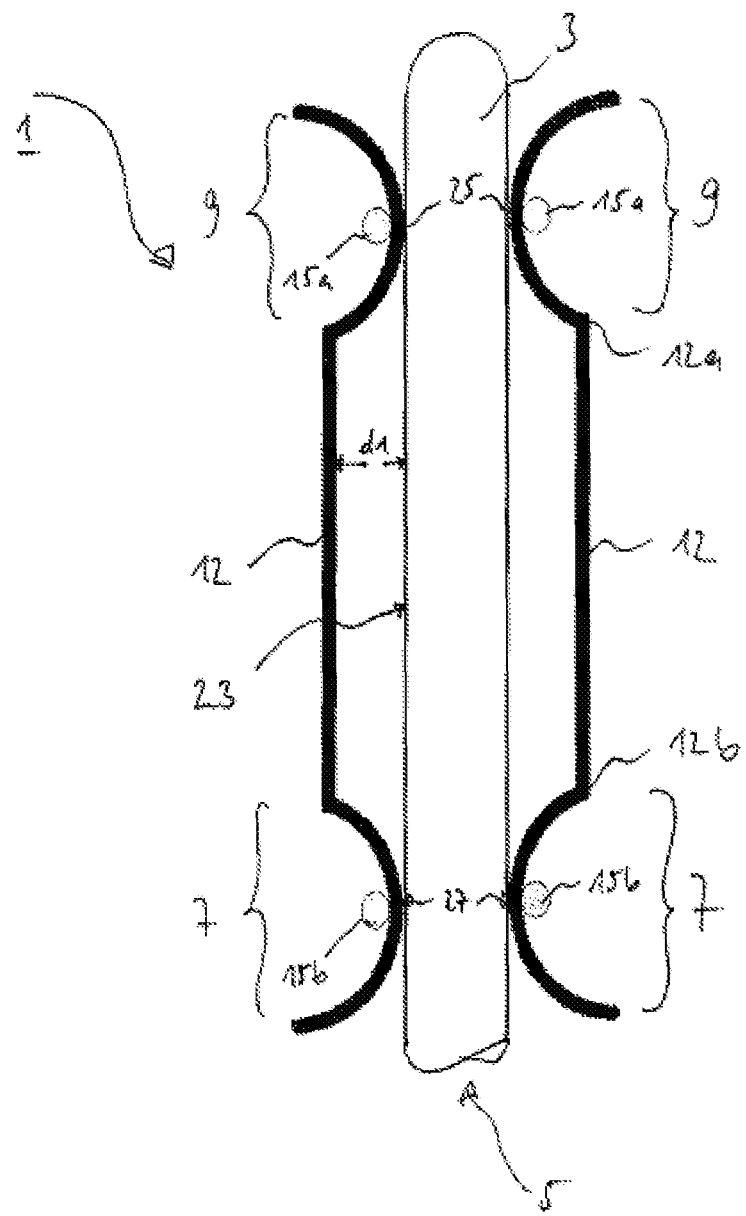
FIG. 1 shows a schematic illustration of an implant according to the invention in a first embodiment.

FIG. 1 shows a schematic illustration of an implant 1 according to the invention in a first embodiment. The implant 1 is crimped onto the outer surface 23 of the tip 3 of a catheter 5. The catheter 5 has a proximal ring 7, a distal ring 9 and posts 12 with proximal and distal ends 12a, 12b. Strings 15a, 15b are guided by means of the distal ring 9 and the proximal ring 7, respectively. The strings 15a, 15b may be used for folding and unfolding of the implant 1 in a controlled manner.

The implant 1 may be a heart valve replacement as is described in WO 2008/029296 A2 or in WO 2009/109348 A1 as referred to above.

As can be seen from FIG. 1, the implant 1 is tightly crimped onto the catheter 5 such that ring-shaped portions 25 and 27 are in contact with the outer surface 23 of the catheter 5. As can also be seen, at least a first gap d1 between the post 12 and the outer surface 23 of the implant 1 is created and/or maintained during crimping. In certain embodiments according to the invention, the first gap d1 has the shape of a tube. In the embodiment of FIG. 1 it is due to the first gap d1 that structures comprised by the implant such as heart leaflets or commissures (both not shown in the figures) may be left unstressed, unpressed unforced and the like upon and after crimping of the entire implant 1 or the implant as such, respectively.

Figure 2:
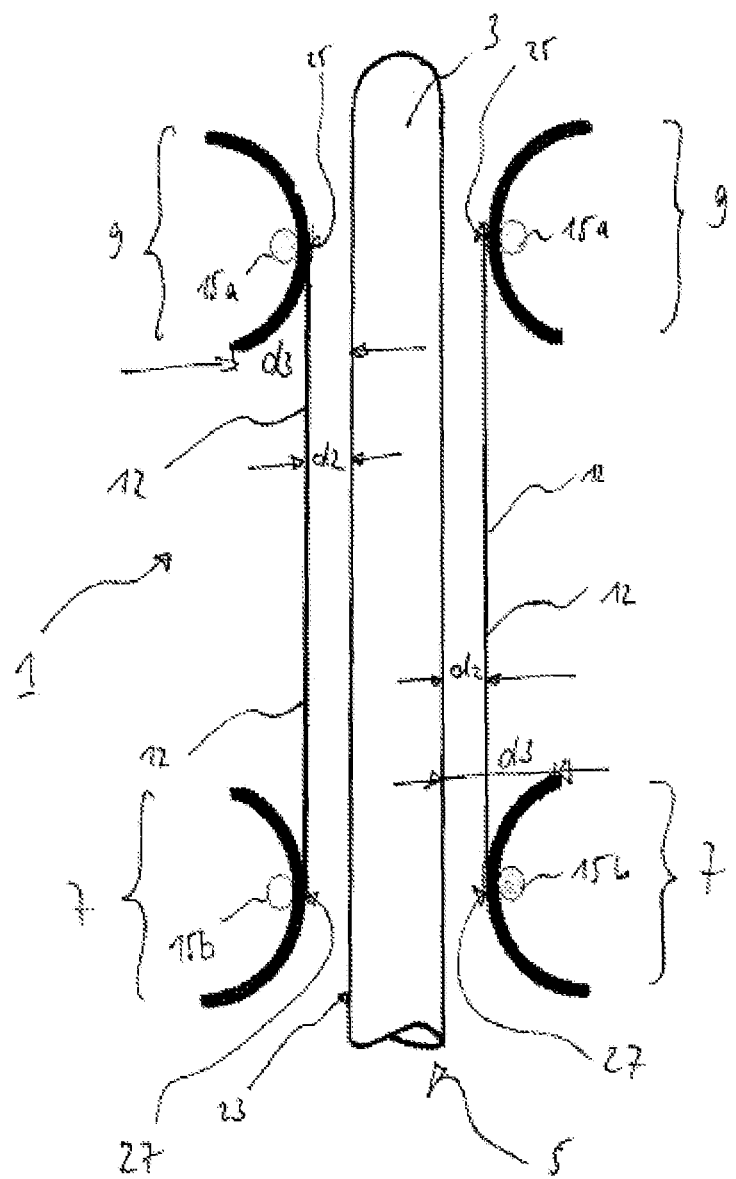
FIG. 2 shows a schematic illustration of an implant according to the invention in a second embodiment.

FIG. 2 shows a schematic illustration of an implant 1 according to the invention in a second embodiment.

In the second embodiment, in contrast to the crimping state shown in FIG. 1 in which the implant 1 is in contact or form fit with the outer surface 23 of the catheter 5 along ring-shaped portions 25 and 27, the implant 1 does not have contact with the outer surface 23 at all. Rather, after completion of the crimping process of implant 1, a second gap d2 remained between the implant 1 (e.g., its post 12 or its ring-shaped portions 25 and 27 of the distal and proximal rings 9, 7) and the outer surface 23 of the catheter. A interconnection between the catheter 5 and the implant 1 needed for delivery of the implant 1 to its implantation site may be achieved by means of the strings 15a, 15b, which are connected to the catheter 5 (interconnection is not shown in FIG. 1 or 2; it can, however be seen in all detail in WO 2008/029296 A2 or in WO 2009/109348 A1 as referred to above). A connection may also be achieved by means of a sleeve (not shown) covering the implant during delivery.

The interconnection between implant 1 and catheter 5 is a more loose one when compared to that achieved by the crimping the result of which is shown in FIG. 1.

As is obvious to the skilled person, structures of the implant 1 such as (not shown) heart valve leaflets may be comprised and housed by the implant 1 during and after crimping of the implant 1 without being stressed, crushed, forced, pushed and/or the like. Gaps d1, d2 and d3 provide sufficient space for such structures such that the implant can be crimped without any adverse effect happening to said structures.

As can be seen from FIG. 2, in contrast to the implant shown in FIG. 1, at least one (or all) of the posts 12 of the implant 1 are arranged such that it is level with the distal and proximal rings 7, 9. Hence, as can be derived from FIG. 2, the method according to the present invention can be carried out with any type of implant. The benefit of the method according to the invention does not depend on the concrete or specific design or embodiment of the implant.

Figure 3:
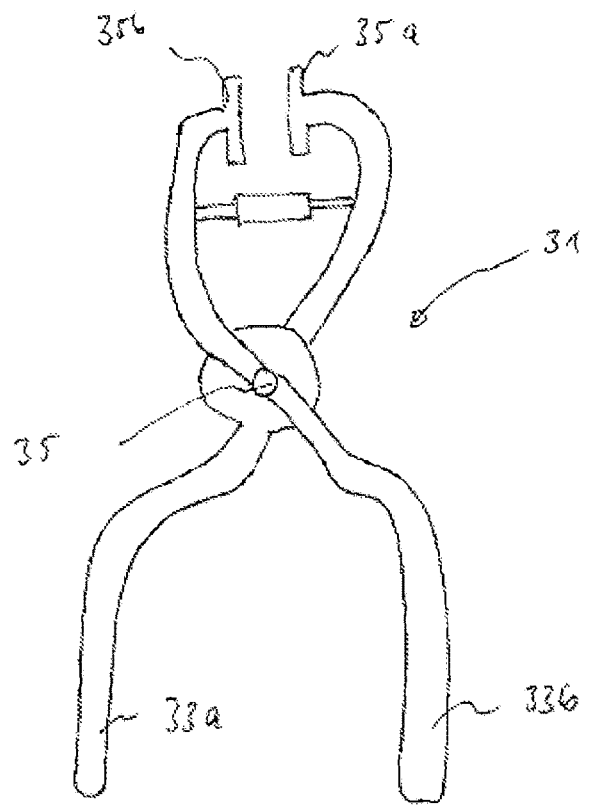
FIG. 3 shows a schematic illustration of a crimping device according to a first embodiment of the invention.

FIG. 3 shows a schematic illustration of a hand-held and hand-operated crimping device 31 according to a first embodiment of the invention.

The crimping device 31 comprises actuators 33a, 33b comprising brackets 35a, 35b for receiving the (not shown) implant for crimping same. The actuators 33a, 33b are connected to each other by means of an articulation or a joint 37. They are further connected to each other by means of a pressure limiting means 39. The pressure limiting means 39 may be adjustable. It limits the pressure exerted to the structure at issue of the implant to the predetermined pressure.

Figure 4:
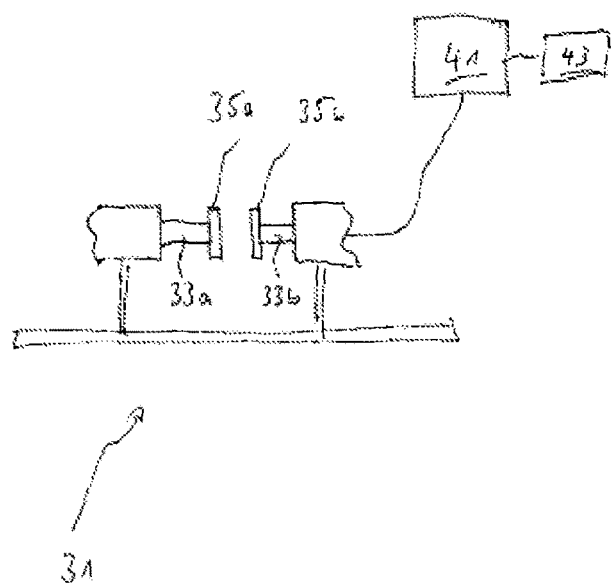
FIG. 4 shows a schematic illustration of a crimping device according to a second embodiment of the invention.

FIG. 4 shows a schematic illustration of a crimping device according to a second embodiment of the invention.

Like the crimping device of FIG. 3, the crimping device 31 comprises actuators 33a, 33b comprising brackets 35a, 35b for receiving the (not shown) implant for crimping the same.

In contrast to the first embodiment, in the second embodiment the crimping device comprises pressure limiting means embodied as controller 41. The controller 41 may be interconnected to an adjusting means 43 for adjusting the maximum pressure exerted to the structure in question of the implant in correspondence to the predetermined pressure.

It is noted that the crimping device according to the invention may have in any embodiment thereof (that is, irrespective of any further features of the crimping devices 31 shown in FIG. 3 or 4) a sensor for measuring the pressure or force exerted on the structure during crimping.

What is claimed is:

1. A method for crimping a medical implant on a catheter, the medical implant comprising:
   a foldable and unfoldable structure having one or more heart valve leaflets or replacements or substitutes thereof, a proximal ring and a distal ring, and
at least one interconnecting element for maintaining a distance between the proximal ring and the distal ring of the implant,
wherein the method comprises:
determining a predetermined pressure;
crimping the medical implant on an outer periphery of the catheter in such a way that the catheter is positioned at a longitudinally central axis of the medical implant, and a gap is maintained between the at least one interconnecting element and the outer periphery of the catheter, and the foldable and unfoldable structure is located in the gap;
measuring a pressure exerted on the foldable and unfoldable structure during crimping of the implant; and
terminating crimping of the implant once the measured pressure has reached or exceeded the predetermined pressure; and
wherein in any steps of the method,
the proximal ring has a first bending portion, the first bending portion having two longitudinal ends located one above another along a direction parallel to the longitudinally central axis and a curved portion between the two longitudinal ends, with the curved portion being convex radially inwardly toward the longitudinally central axis;
the distal ring is spaced apart from the proximal ring along the longitudinally central axis, the distal ring having a second bending portion, the second bending portion having two longitudinal ends located one above another along a direction parallel to the longitudinally central axis and a curved portion between the two longitudinal ends, with the curved portion being convex radially inwardly toward the longitudinally central axis;
the at least one interconnecting element is arranged between the proximal ring and the distal ring, and connects the first bending portion to the second bending portion, the at least one interconnecting element being disposed generally parallel to the longitudinally central axis along an entire length of the at least one interconnecting element; and
the curved portion of the first bending portion and the curved portion of the second bending portion are both located radially closer to the longitudinally central axis than the interconnecting element.

2. The method according to claim 1, wherein the predetermined pressure is 0 N per square millimetre, and the method further comprises
terminating crimping of the implant once the measured pressure has reached or exceeded 0 N per square millimetre.

3. The method according to claim 1, wherein the predetermined pressure is 5 N per square millimetre, and the method further comprises
terminating crimping of the implant once the measured pressure has reached or exceeded 5 N per square millimetre.

4. The method according to claim 1, wherein the method further comprises
placing a force sensor in direct contact with the structure before the crimping procedure.

5. A method for crimping a medical implant on a catheter, the medical implant comprising:
a foldable and unfoldable structure having one or more heart valve leaflets or replacements or substitutes thereof,
a proximal ring and a distal ring, and
at least one interconnecting element for maintaining a distance between the proximal ring and the distal ring of the implant,
wherein the method comprises:
determining a predetermined pressure;
crimping the medical implant on an outer periphery of the catheter in such a way that the catheter is positioned at a longitudinally central axis of the medical implant, and a gap is maintained between the at least one interconnecting element and the outer periphery of the catheter, and the foldable and unfoldable structure is located in the gap;
measuring a pressure exerted on the foldable and unfoldable structure during crimping of the implant; and
terminating crimping of the implant once the measured pressure has reached or exceeded the predetermined pressure; and
wherein in any steps of the method,
the proximal ring has a C-shaped first bending portion, the first bending portion having a middle section protruding radially toward the longitudinally central axis;
the distal ring is spaced apart from the proximal ring along the longitudinally central axis, the distal ring having a C-shaped second bending portion, the second bending portion having a middle section protruding radially toward the longitudinally central axis;
the at least one interconnecting element is arranged between the proximal ring and the distal ring, and connects the first bending portion to the second bending portion, the at least one interconnecting element being disposed generally parallel to the longitudinally central axis along an entire length of the at least one interconnecting element; and
the middle section of the first bending portion and the middle section of the second bending portion are both located radially closer to the longitudinally central axis than the interconnecting element.

6. The method according to claim 5, wherein the predetermined pressure is 0 N per square millimetre, and the method further comprises
terminating crimping of the implant once the measured pressure has reached or exceeded 0 N per square millimetre.

7. The method according to claim 5, wherein the predetermined pressure is 5 N per square millimetre, and the method further comprises
terminating crimping of the implant once the measured pressure has reached or exceeded 5 N per square millimetre.

8. The method according to claim 5, wherein the method further comprises placing a force sensor in direct contact with the structure before the crimping procedure.

* * * * *